United States Patent [19]

Oita

[11] 4,409,336
[45] Oct. 11, 1983

[54] METHOD OF ANALYSIS FOR DETERMINING VERY LOW SULFUR LEVELS IN VOLATILIZABLE SAMPLES

[75] Inventor: Jack I. Oita, Wheaton, Ill.

[73] Assignee: Standard Oil Company (Indiana), Chicago, Ill.

[21] Appl. No.: 385,795

[22] Filed: Jun. 7, 1982

Related U.S. Application Data

[63] Continuation-in-part of Ser. No. 234,712, Feb. 17, 1981, abandoned.

[51] Int. Cl.$^3$ .................. G01N 31/12; G01N 31/16
[52] U.S. Cl. ............................. 436/123; 436/122; 436/158; 436/160; 204/1 T; 422/80
[58] Field of Search ............... 436/123, 122, 160, 158, 436/155; 422/78, 80; 423/244 R; 23/230 PC, 232 R; 204/1 T

[56] References Cited

U.S. PATENT DOCUMENTS

| | | | |
|---|---|---|---|
| 1,205,724 | 11/1916 | Fairlie | 23/232 R |
| 1,634,331 | 7/1927 | Mase | 23/232 R |
| 2,669,504 | 2/1954 | Halvorson et al. | 23/232 R |
| 3,501,897 | 3/1970 | Helden et al. | 423/244 R X |
| 3,838,969 | 10/1974 | Dugan | 436/123 |
| 4,053,281 | 10/1977 | Carter | 436/160 X |
| 4,170,627 | 10/1979 | Ginger | 423/244 R X |
| 4,172,705 | 10/1979 | Castro et al. | 422/80 X |

FOREIGN PATENT DOCUMENTS 790217 2/1958 United Kingdom ................ 436/158

OTHER PUBLICATIONS

Kirsten; Analytical Chemistry, vol. 51, No. 8 (Jul. 1979), pp. 1173–1179.

Primary Examiner—Kenneth M. Schor
Attorney, Agent, or Firm—Lansing M. Hinrichs; William T. McClain; William H. Magidson

[57] ABSTRACT

A new method is disclosed for determining sulfur levels in liquid or solid samples. The method is capable of accurate determination of sulfur content at sub-parts per million levels. The method and apparatus utilize high temperature oxidation of the samples to form sulfur oxides, absorption of the sulfur oxides on copper oxide as copper sulfate, thermal decomposition of the sulfate to convert sulfur present to sulfur dioxide which is evolved and coulometric titration to measure the quantity of evolved sulfur dioxide from which sulfur content of the sample can be calculated.

6 Claims, 3 Drawing Figures

FIG. 2
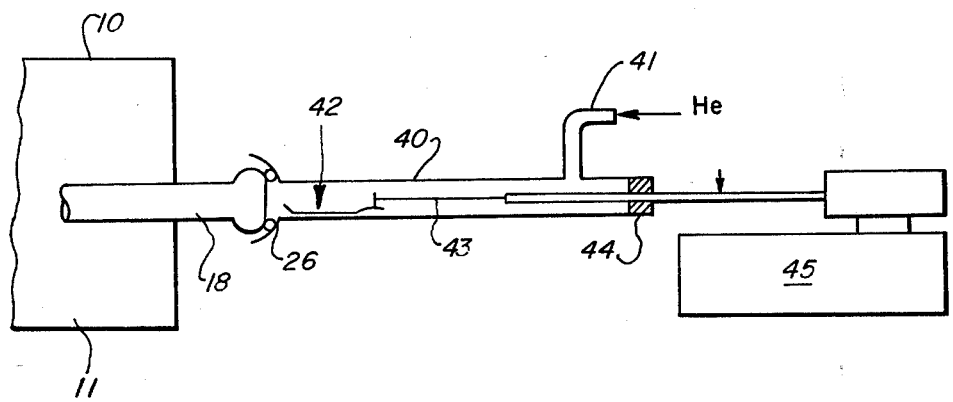
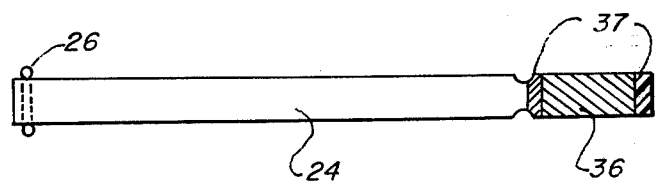
FIG. 3

METHOD OF ANALYSIS FOR DETERMINING VERY LOW SULFUR LEVELS IN VOLATILIZABLE SAMPLES

BACKGROUND OF THE INVENTION

Field of the Invention

This application is a continuation-in-part of my co-pending patent application Ser. No. 234,712 filed Feb. 17, 1981 and now abandoned.

This invention relates to the field of quantitative chemical analysis and more particularly to a novel method for determining the sulfur content of liquid or solid samples at sub-parts per million by weight (sub-ppm) levels. The method of this invention utilizes a bed of particulate cupric oxide downstream of a sample combustion zone to accumulate sulfur oxides during combustion of the sample as copper sulfate ($CuSO_4$) and subsequently to release the accumulated sulfur as sulfur dioxide ($SO_2$) for quantitative determination preferably by coulometric titration with iodine.

Determination of the presence of sub-ppm levels of sulfur in materials such as petroleum refinery feedstocks, intermediates, and products has become increasingly important in recent years, but the heretofore available methods of sulfur analysis are generally not adequate at sub-ppm levels.

The Wickbold method which is described in Angewandt Chemie 69, 530 (1957) uses an oxy-hydrogen burner to form oxides of sulfur which are determined by either spectrophotometric, nephelometric or turbidimetric procedures. By burning very large samples, it is possible to achieve a precision of 0.2 ppm of sulfur, but the total elapsed time to analyze a sample is about three hours.

A Raney nickel reduction method which has been developed by Granatelli—see Anal. Chem. 31, 434 (1959)—and improved by Pitt and Rupprect—see Fuel 43, 417 (1964)—permits the determination of sulfur down to 0.1 ppm in petroleum distillate fractions. However, this method also requires an elapsed time of about three hours and suffers from the limitation that it does not determine oxidized forms of sulfur such as sulfonic acids.

A hydrogenolysis method utilizing a Houston-Atlas Analyzer has been described by Drushel in Analytical Chemistry, Volume 50, page 76 (1978). In this method the sample is contacted with a stream of hydrogen in a furnace to convert sulfur compounds to hydrogen sulfide. The thus formed hydrogen sulfide is measured photometrically by measuring the rate of blackening of a lead acetate-impregnated paper strip. The method is reported to be sensitive for determining sulfur at sub-ppm levels.

Oxidative coulometry is currently practiced for sulfur determination. In oxidative coulometry, the sample is burned in oxygen and the generated sulfur dioxide is coulometrically titrated with iodine, as shown in the following reactions.

$$Sample + O \rightarrow SO_2 + SO_3 + CO_2 + H_2O \quad (1)$$

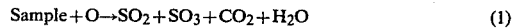

$$SO_2 + I_2 + H_2O \rightarrow SO_3 + 2I^- 2H^+ \quad (2)$$

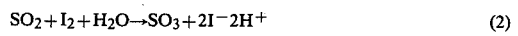

However, there are three main problems with this method. First, although the $SO_2/SO_3$ equilibrium in reaction (1) is generally 90% in favor of $SO_2$ at the 1000° C. combustion temperature, it varies with temperature, flow rate, and the type and amount of sulfur. For trace samples, it can be as low as 50%. This effect produces low results.

The second problem with the coulometric approach is that reaction (2) of $I_2$ with $SO_2$ is not selective. If olefins are formed during the combustion, they consume iodine leading to high results. In order to minimize olefin formation, the sample must be burned slowly. However, this is unsatisfactory in two respects: (a) the large sample size required for trace analysis makes the combustion time excessive and (b) the iodine generation is so drawn out that accuracy of its measurement is greatly reduced. Attempts have been made to resolve the latter problem by not turning on the coulometer until combustion is complete. Although a sharp peak is thus obtained, there is no way to compensate for the iodine lost from the cell by vaporization. Thus, in order to maintain the proper iodine/iodide equilibrium when the coulometer is turned on, iodine is generated which again leads to high results. Too rapid combustion can lead to soot formation which can adsorb $SO_2$ and cause low results.

Another problem which may occur arises from the presence of oxidizing agents such as chlorine or oxides of nitrogen which may be liberated during combustion of the sample. When such agents are passed through the coulometric cell they produce a negative peak and may lead to low results. U.S. Pat. No. 4,172,705 to Castro et al. discloses scrubbing the oxidized sample components with a tin-containing agent prior to coulometric titration thereof.

Thus, depending upon the combustion conditions and type of sample, results can be high or low. Although many of these errors are not important at greater than 1 ppm sulfur levels, they can become quite significant below 1 ppm.

The following reactions between copper oxide and sulfur oxides have been known for some time and are described by Pella and Columbo in Microchimica Acta [Wien] 1978 I, pages 271–286:

$$SO_2 + 3CuO \rightarrow Cu_2O + CuSO_4 \quad (3)$$

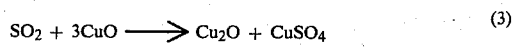

$$SO_3 + CuO \rightarrow CuSO_4 \quad (4)$$

$$840° C.$$

$$CuSO_4 \rightarrow CuO + SO_2 + \tfrac{1}{2}O_2 \quad (5)$$

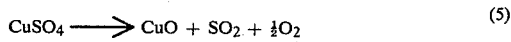

Pella and Columbo disclose a gas chromatography method for simultaneous C—H—N and S microdetermination. In their method a sample is oxidized catalytically in a stream of helium and oxygen and conducted over a bed of copper oxide maintained at 850° C. and which has been reduced by carbon monoxide and hydrogen treatment to copper. The purpose of this step is to remove all oxygen from the stream and prevent the formation of $SO_3$ or $H_2SO_4$ from $SO_2$. There is no absorption of sulfur oxides by the copper-copper oxide bed, and they pass with the helium to the gas chromatograph.

SUMMARY OF THE INVENTION

This invention provides a method of analysis for determining very low sulfur levels in volatilizable samples.

In a preferred embodiment of this invention, an iodometric analysis is utilized for determining very low levels of sulfur in volatilizable samples which contain sulfur and hydrocarbons convertible at least in part to unsaturated hydrocarbons by oxidative pyrolysis is provided. The method comprises:

(a) contacting a sample of known quantity with a flowing stream of a carrier gas and oxygen at a temperature in the range of 800° C. to 1000° C. and sufficiently high to pyrolyze and volatilize the sample and to effect the oxidation of oxidizable sulfur containing components therein to sulfur dioxide and sulfur trioxide;

(b) conveying the pyrolyzed and volatilized components of said sample in the flowing stream of carrier gas through a fixed bed of cupric oxide maintained at a temperature in the range of about 650° C. to about 800° C., whereby, sulfur dioxide and sulfur trioxide are quantitatively captured by the cupric oxide as copper sulfate and unsaturated hydrocarbons are oxidized so as to be non-interfering in the iodometric analysis;

(c) after all of the sulfur oxides are quantitatively captured, raising the temperature of the cupric oxide to about 840° C. to decompose the copper sulfate and liberate sulfur dioxide, the rate of temperature increase being sufficiently high to complete the decomposition and liberation within a period of time of from about one to five minutes and substantially less than the time of pyrolysis and volatilization set forth in (a) above; and (d) determining by coulometric iodometric titration the amount of sulfur dioxide which is liberated to determine the sulfur content of the sample by passing the carrier gas containing the liberated sulfur dioxide through an iodometric titration cell.

The method of this invention may, if desired, be varied by substituting an infrared or a gas chromatograph determination or other conventional determination for the iodometric titration. If this is done the advantage of having all the evolved sulfur in the form of sulfur dioxide is important in that in infra-red determinations of the sulfur dioxide and sulfur trioxide indications overlap so that if both are present an accurate determination cannot be made. Similarly, in gas chromatography applications separation of these components into distinct peaks is problematical. Whatever determination is utilized the advantage of the method of this invention of concentrating the evolution of the sulfur within a period substantially less than the period of oxidative pyrolysis and volatilization produces ultimate determinations of higher accuracy.

BRIEF DESCRIPTION OF THE DRAWINGS

FIG. 2 is a schematic view of a sample feeding apparatus for handling solid or very viscous samples to be analyzed by the method of this invention.

FIG. 3 is a side view showing a preferred arrangement for supporting a bed of cupric oxide within a quartz tube which is receivable in the furnace portion of the apparatus shown in FIG. 1.

DETAILED DESCRIPTION OF THE INVENTION

Figure 1:
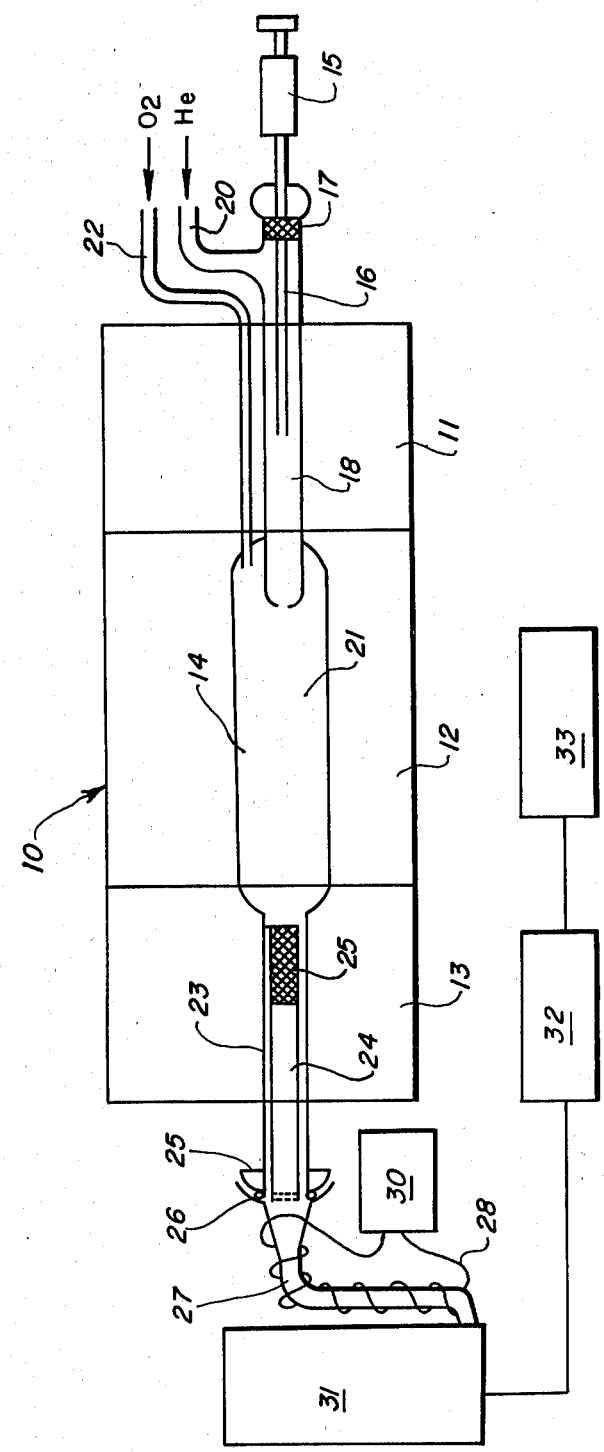
FIG. 1 is a schematic view of a system of apparatus for carrying out the method of this invention to determine the sulfur content of volatile liquid samples.

The method of this invention for determining very low sulfur levels in volatilizable samples can best be understood by describing first a preferred system of apparatus for carrying out the method. In FIG. 1, there is shown a furnace 10 which is preferably an electric furnace having three heating zones 11, 12, and 13 which may be selectively heated to predetermined temperatures. Extending longitudinally through the three heating zones there is an assembly of quartz tubes 14 having the configuration shown. A syringe 15 having an injection tube 16 which is insertable through a septum 17 into the sample inlet section 18 of the quartz tube assembly 14 is provided for injecting liquid samples. A quartz tube 20 opening into the inlet section 18 is provided for introducing a carrier stream of helium or other inert gas for conducting the vaporized sample into the combustion zone 21 of the tube assembly 14.

A quartz tube 22 connected to a supply of oxygen or other combustion supporting gas extends from outside the furnace 10, through the heating zone 11 and into the combustion zone 21. The outlet end of the combustion zone 21 is connected to a smaller diameter quartz tube 23 leading out of the furnace 10. A slightly smaller diameter quartz tube 24, whose function is to support a bed of cupric oxide 25, is received within tube 23. The end of tube 23 projects outside of the furnace 10 to a bell and spigot joint 25 having a silicone seal ring 26.

From the bell and spigot joint 25 a tube 27, traced with electrical heating tape 28 supplied with electrical current from power source 30, extends to iodometric titration cell 31 or other analyzer. The purpose of the heating tape is to prevent any condensation of combustion products in tube 27. The iodometric titration cell 31 is electrically connected with a conventional coulometer 32 whose output is transmitted to recorder 33.

With the exception of the quartz tube 24 containing the bed of cupric oxide the above described apparatus may be readily assembled from commercially available equipment. The following apparatus has been utilized quite successfully.

Dohrmann S-300 Furnace
Dohrmann T-300P Titration Cell
Dohrmann C-200 or C-300 Microcoulometer
Sage Model 341 Syringe Pump The quartz cupric oxide containing tube 24 is shown in detail in FIG. 3. Tube 24 is necked in at a point 34 a short distance from its inlet end 35 to provide a retaining means to prevent the bed of cupric oxide 36 from being carried further into tube 24 by flowing gases. Quartz wool pads 37 are provided at each end of the cupric oxide bed 36 serving as retainers. The preferred copper oxide is reagent grade cupric oxide (CuO) in wire form, 1/16 to ⅛ inches (1.6 to 3.2 millimeters) in length. Before being installed in the tube the cupric oxide is preferably sieved to remove powder. The dimensions of a tube suitable for use with the Dohrmann S-300 furnace are as follows:

Outside diameter: 5/16 inch (7.9 mm)
Length: 5 inches (127 mm)
Distance to neck: 1 inch (25.4 mm)

Thus the cupric oxide bed 36 is slightly less than one inch (25.4 mm) in length.

The iodometric titration cell 31 is preferably conventional in design being equipped with platinum reference, sensor and generator electrodes (not shown). The cell is charged with a solution containing iodine and potassium iodide which is used to titrate sulfur dioxide conducted into the cell through tube 27. The coulometer 32 which is also preferably conventional measures the quantity of electricity produced in the cell as iodine is reduced to iodide by the sulfur dioxide within the cell. The recorder 33 is preferably a conventional integrating type preferably with digital readout.

The analytical method of this invention can best be understood by the following description of the operation of the above-described apparatus.

A flow of a carrier gas is initiated through tube 20. The carrier gas may be helium, argon, nitrogen or even air, if desired, but helium is usually preferred because of its availability in convenient pure form. When the flow of the carrier gas has been established and the furnace temperatures stabilized, a stream of oxidizing gas, preferably pure oxygen, is initiated through tube 22. It will be appreciated by those familiar with the art that in some cases air alone can be employed as both the carrier gas and the source of oxygen. However, because of the ready availability and reliability as to purity of compressed gases in cylinders it is preferable to employ pure grades of cylinder oxygen and helium. This, of course, is particularly important when very small amounts of sulfur are to be detected and analyzed. When helium and oxygen are employed in the above-described apparatus the helium flow rate can be set at about 30 ml/minute and the oxygen flow rate at about 80 ml/minute.

Before the start of the analysis and with gas flow established, the three zones of the furnace 10 are heated to elevated temperatures. The temperature of the inlet zone 11 should be sufficiently high to insure pyrolysis and vaporization of the sample and preferably be between about 700° C. and 900° C. The temperature of the center zone 12 should be maintained sufficiently high to insure complete combustion of the sulfur containing components in the sample and in the range of about 800° C. to about 1000° C. and preferably about 900° C. The temperature in the exit zone 13 is in the range of about 650° C. to 800° C. and preferably about 700° C. In no event should the temperature in the exit zone exceed 800° C. during the initial stage of the analysis, for above this temperature sulfur oxides will not combine with the cupric oxide 25 to form copper sulfate and this step is critical to the operation of the method of analysis of the invention. In practice it is preferred to initially heat the third zone to 900° C. with gas flow established to insure that any sulfur oxides which might be present from previous determinations are evolved and then to drop the temperature to 700° C. before starting the analysis.

The syringe 15 is filled in the usual manner with a known quantity of the sample to be analyzed. Measurement of the sample quantity may be by weight or preferably by volume if the syringe is calibrated. A convenient sample size when liquids are to be analyzed is one milliliter although larger samples may be utilized if desired. A convenient sample size in the case of solid samples is about 100 milligrams. In the case of a one milliliter liquid sample an injection time of about twenty minutes is employed. Injection is accomplished by inserting the injection tube 16 of the syringe 15 through septum 17. Because of the relatively long time required to slowly inject the sample a conventional automatic device for slowly driving the syringe piston forward is usually preferred. After the sample has been fully injected, flow of carrier gas and oxygen is allowed to continue for a short period of time which can be about one to five minutes to insure that interfering effects of oxidizing compounds have been dissipated.

The exit zone 13 of the furnace is then heated to a temperature which must be above 840° C. and preferably is about 900° C. to decompose the copper sulfate which has been formed on the surface of the cupric oxide bed 25. Heating of exit zone 13 to decomposition temperature is preferably accomplished as rapidly as the apparatus will permit in order to decompose the copper sulfate in a very short period of time. The shorter the period the more peaking of sulfur dioxide elution occurs and the more accurate will be the resulting determination whether it be an iodometric titration gas chromatography, infrared or other determination. The period of time for heating the copper oxide bed to evolve the sulfur dioxide can be as short as one minute and should, for best results, not be more than about five minutes. Moreover, the period should be substantially shorter than the time required for the oxidative pyrolysis and volatilization, preferably about one tenth as long and in no event more than about one fourth as long if enhanced determination accuracy is to be achieved.

The iodometric titration occurs in cell 31 which is preferably a conventional oxidative coulometric cell having digital readout in nanograms of sulfur, although a strip chart recorder is useful to monitor the elution of the sulfur dioxide peak. If a nondigital coulometer is used, an integrating recorder must be used and the area of the sulfur peak must be compared with the area of the sulfur peak obtained with a known sulfur standard. A blank should be run periodically and the blank correction is preferably applied in the calculations. The sulfur content is calculated as follows:

$$\frac{S_s - S_b}{\text{vols.} \times \text{density}} = \text{ppm S}$$

where:
 $S_s$ = nanograms of sulfur found in sample
 $S_b$ = nanograms of sulfur in blank
 vols. = volume of sample in microliters
 density = density of sample To summarize the method described above involves two steps. First, the sample is burned and the products of combustion are passed over cupric oxide at 700° C., a temperature at which both $SO_2$ and $SO_3$ form stable $CuSO_4$. Any partially oxidized hydrocarbons are oxidized by the cupric oxide eliminating both olefin and soot formation. Any oxidizing compounds such as chlorine and nitrogen oxides are permitted to pass through the cell without measuring their effect and, when the sample has been completely burned and the coulometric cell is at equilibrium, the $CuO/CuSO_4$ zone is rapidly heated to 900° C. over a period of about one to five minutes to liberate the sulfur as $SO_2$ providing accurate measurement. Thus, problems formerly associated with oxidative coulometry for trace sulfur determination have been resolved.

In FIG. 2 of the drawings a convenient accessory for adapting the apparatus of FIG. 1 to receive solid samples is shown. The accessory comprises a tube 40, preferably quartz, adapted to connect in sealed relationship with tube 18 which extends into the inlet zone 11 of furnace 10. Tube 40 has an inlet 41 for carrier gas which is injected at this point when solid samples are analyzed rather than at 20. A platinum sample boat 42 is slidably received within tube 40 and is connected to push rod 43 which extends outside of tube 40 through septum 44. Push rod 44 is arranged to be actuated by the syringe actuation mechanism 45 which can be the same mechanism utilized to activate the syringe 15 when liquid samples are analyzed.

To analyze a sample, a known weight is deposited in boat 42, preferably spread out the length of the boat and not heaped, and the boat is inserted in tube 40 connected to rod 43. The flow of carrier gas is established and, with furnace 10 up to temperature, the actuator mechanism 45 then is employed to slowly move the boat and sample into the inlet zone 11 of the furnace 10 where the sample vaporizes.

Sample sizes and rates of volatilization are important to accurate analysis. As has been stated a liquid sample of one milliliter requires about 20 minutes for vaporization. If the sample to be analyzed contains a relatively larger amount of sulfur, about 1 ppm, reducing the sample size to about 100 microliters will permit reduction of vaporization time to about two minutes and still produce good results. For solid samples a practical size is 100 milligrams with a time of insertion of five minutes.

In summary, there is provided a highly sensitive and accurate method of determining sulfur in organic samples in the sub-ppm range. Tests have shown that the relative standard deviation is less than 10% for samples containing 0.04 to 1 ppm sulfur. The lowest limit of practical detection is about 0.01 ppm. This method can be used for samples that contain appreciable amounts of chlorine or nitrogen which interfere in the normal coulometric method.

Various changes and modifications such as will present themselves to those familiar with the art may be made without departing from the spirit of this invention whose scope is defined by the following claims.

I claim:

1. An iodometric method of analysis for determining very low levels of sulfur in volatilizable samples which contain sulfur and hydrocarbons which are convertible at least in part to unsaturated hydrocarbons by pyrolysis, which method comprises:
   (a) contacting a sample of known quantity with a flowing stream of a carrier gas and oxygen at a temperature in the range of 800° C. to 1000° C. and sufficiently high to pyrolyze and volatilize the sample and to effect the oxidation of oxidizable sulfur containing components therein to sulfur dioxide and sulfur trioxide;
   (b) conveying the pyrolyzed and volatilized components of said sample in the flowing stream of carrier gas through a fixed bed of cupric oxide maintained at a temperature in the range of about 650° C. to 800° C., whereby, sulfur dioxide and sulfur trioxide are quantitatively captured by the cupric oxide as copper sulfate and unsaturated hydrocarbons are oxidized so as to be noninterfering in an iodometric analysis;
   (c) after all of the sulfur oxides are quantitatively captured, removing the stream of carrier gas together with the oxidized unsaturated hydrocarbons from contact with said fixed bed, and then raising the temperature of the cupric oxide above 840° C. to decompose said copper sulfate and liberate sulfur dioxide, the rate of temperature increase being sufficiently high to complete the decomposition and liberation within a perod of time substantially less than the time of pyrolysis and volatilization in step (a); and
   (d) determining by iodometric titration the amount of sulfur dioxide which is liberated to determine the sulfur content of said sample by passing the carrier gas containing the liberated sulfur dioxide through an iodometric titration cell.

2. A method of analysis for determining very low levels of sulfur in volatilizable samples which contain sulfur and hydrocarbons which are convertible at least in part to unsatureated hydrocarbons by pyrolysis, which method comprises:
   (a) contacting a sample of known quantity with a flowing stream of a carrier gas and oxygen at a temperature in the range of 800° C. to 1000° C. and sufficiently high to pyrolyze and volatilize the sample and to effect the oxidation of oxidizable sulfur containing components therein to sulfur dioxide and sulfur trioxide;
   (b) conveying the pyrolyzed and volatilized components of said sample in the flowing stream of carrier gas through a fixed bed of cupric oxide maintained at a temperature in the range of about 650° C. to 800° C., whereby, sulfur dioxide and sulfur trioxide are quantitatively captured by the cupric oxide as copper sulfate and unsaturated hydrocarbons are oxidized so as to be noninterfering in an iodometric analysis;
   (c) after all of the sulfur oxides are quantitatively captured, removing the stream of carrier gas together with the oxidized unsaturated hydrocarbons from contact with said fixed bed, and then raising the temperature of the cupric oxide above 840° C. to decompose said copper sulfate and liberate sulfur dioxide; and
   (d) determining by iodometric titration the amount of sulfur dioxide which is liberated to determine the sulfur content of said sample.

3. The method of claim 2 wherein the liberated sulfur dioxide is determined by coulometric iodometric titration.

4. The method of claim 2 wherein the carrier gas is helium.

5. The method of claim 2 wherein the capture of the sulfur oxides is effected at a temperature of about 700° C. and the decomposition of the copper sulfate is effected at a temperature of about 900° C.

6. The method of claim 1 wherein a sample having a sulfur level of less than one part per million by weight is analyzed.

* * * * *